(12) United States Patent
Coburn et al.

(10) Patent No.: US 7,449,599 B2
(45) Date of Patent: Nov. 11, 2008

(54) PHENYL CARBOXAMIDE COMPOUNDS USEFUL AS BETA-SECRETASE INHIBITORS FOR THE TREATMENT OF ALZHEIMER'S DISEASE

(75) Inventors: Craig A. Coburn, Royersford, PA (US); Thomas G. Steele, Schwenksville, PA (US); Joseph P. Vacca, Telford, PA (US); David Allen Annis, Jr., Cambridge, MA (US); Gergely M. Makara, Norwood, MA (US); Huw M. Nash, Cambridge, MA (US); Praveen K. Tadikonda, Norwood, MA (US); Tong Wang, Cambridge, MA (US)

(73) Assignee: Merck + Co Inc., Rahway, NJ (US)

( * ) Notice: Subject to any disclaimer, the term of this patent is extended or adjusted under 35 U.S.C. 154(b) by 185 days.

(21) Appl. No.: 11/579,049

(22) PCT Filed: May 9, 2005

(86) PCT No.: PCT/US2005/015949

§ 371 (c)(1),
(2), (4) Date: Oct. 27, 2006

(87) PCT Pub. No.: WO2005/113484

PCT Pub. Date: Dec. 1, 2005

(65) Prior Publication Data

US 2007/0254958 A1    Nov. 1, 2007

Related U.S. Application Data

(60) Provisional application No. 60/570,687, filed on May 13, 2004.

(51) Int. Cl.
| | |
|---|---|
| C07C 233/05 | (2006.01) |
| C07C 233/65 | (2006.01) |
| C07C 305/18 | (2006.01) |
| C07C 255/50 | (2006.01) |
| A61K 31/16 | (2006.01) |
| A61K 31/255 | (2006.01) |
| A61K 31/275 | (2006.01) |

(52) U.S. Cl. .................. 564/156; 564/153; 558/52; 558/415; 514/518; 514/522; 514/616

(58) Field of Classification Search ............... 564/153, 564/156; 558/52, 415; 514/518, 522, 616
See application file for complete search history.

(56) References Cited

FOREIGN PATENT DOCUMENTS

| WO | WO 96/08483 | 3/1996 |
|---|---|---|
| WO | WO 03/106405 | 12/2003 |
| WO | WO 2005/005374 | 1/2005 |

OTHER PUBLICATIONS

Craig A. Coburn et al., "Identification of a Small Molecule Nonpeptide Active Beta-Secretase . . . ," J. Med. Chem., vol. 47, pp. 6117-6119 (2004).
Shawn J. Stachel et al., "Structure-Based Design of Potent and Selective Cell-Permeable Inhibitors of Human Beta-Secretase (BACE-1)," J. Med. Chem., vol. 47, pp. 6447-6450 (2004).

*Primary Examiner*—Shailendra Kumar
(74) *Attorney, Agent, or Firm*—William Krovatin; John C. Todaro

(57) ABSTRACT

The present invention is directed to phenyl carboxamide compounds which are inhibitors of the beta-secretase enzyme and that are useful in the treatment of diseases in which the beta-secretase enzyme is involved, such as Alzheimer's disease. The invention is also directed to pharmaceutical compositions comprising these compounds and the use of these compounds and compositions in the treatment of such diseases in which the beta-secretase enzyme is involved.

14 Claims, No Drawings

PHENYL CARBOXAMIDE COMPOUNDS USEFUL AS BETA-SECRETASE INHIBITORS FOR THE TREATMENT OF ALZHEIMER'S DISEASE

CROSS-REFERENCE TO RELATED APPLICATIONS

This application claims priority under 35 U.S.C. § 119(e) from U.S. provisional application Ser. No. 60/570,687, filed May 13, 2004, which claims benefit of 60/570,687, filed May 13, 2004.

REFERENCE TO JOINT RESEARCH AGREEMENT

This invention was made as a result of activities undertaken within the scope of a Joint Research Agreement between Merck & Co., Inc. and NeoGenesis, Inc.

BACKGROUND OF THE INVENTION

Alzheimer's disease is characterized by the abnormal deposition of amyloid in the brain in the form of extra-cellular plaques and intra-cellular neurofibrillary tangles. The rate of amyloid accumulation is a combination of the rates of formation, aggregation and egress from the brain. It is generally accepted that the main constituent of amyloid plaques is the 4 kD amyloid protein (βA4, also referred to as Aβ, β-protein and βAP) which is a proteolytic product of a precursor protein of much larger size. The amyloid precursor protein (APP or AβPP) has a receptor-like structure with a large ectodomain, a membrane spanning region and a short cytoplasmic tail. The Aβ domain encompasses parts of both extra-cellular and transmembrane domains of APP, thus its release implies the existence of two distinct proteolytic events to generate its $NH_2$— and COOH-termini. At least two secretory mechanisms exist which release APP from the membrane and generate soluble, COOH-truncated forms of APP ($APP_s$). Proteases that release APP and its fragments from the membrane are termed "secretases." Most $APP_s$ is released by a putative α-secretase which cleaves within the Aβ protein to release α-$APP_s$ and precludes the release of intact Aβ. A minor portion of $APP_s$ is released by a β-secretase ("β-secretase"), which cleaves near the $NH_2$-terminus of APP and produces COOH-terminal fragments (CTFs) which contain the whole Aβ domain.

Thus, the activity of β-secretase or β-site amyloid precursor protein-cleaving enzyme ("BACE") leads to the abnormal cleavage of APP, production of Aβ, and accumulation of β amyloid plaques in the brain, which is characteristic of Alzheimer's disease (see R. N. Rosenberg, Arch. Neurol., vol. 59, September 2002, pp. 1367-1368; H. Fukumoto et al, Arch. Neurol., vol. 59, September 2002, pp. 1381-1389; J. T. Huse et al, J. Biol. Chem., vol 277, No. 18, issue of May 3, 2002, pp. 16278-16284; K. C. Chen and W. J. Howe, Biochem. Biophys. Res. Comm, vol. 292, pp 702-708, 2002). Therefore, therapeutic agents that can inhibit β-secretase or BACE may be useful for the treatment of Alzheimer's disease.

The compounds of the present invention are useful for treating Alzheimer's disease by inhibiting the activity of β-secretase or BACE, thus preventing the formation of insoluble Aβ and arresting the production of Aβ.

SUMMARY OF THE INVENTION

The present invention is directed to phenyl carboxamide compounds useful as inhibitors of the β-secretase enzyme, and are useful in the treatment of diseases in which the β-secretase enzyme is involved, such as Alzheimer's disease. The invention is also directed to pharmaceutical compositions comprising these compounds, and the use of these compounds and compositions in the treatment of such diseases in which the β-secretase enzyme is involved.

DETAILED DESCRIPTION OF THE INVENTION

The present invention is directed to compounds of formula (I):

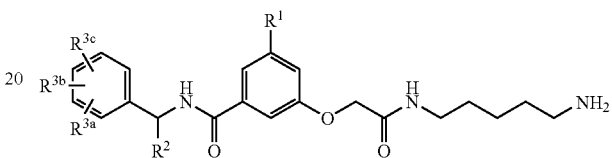

wherein
$R^1$ is selected from the group consisting of:

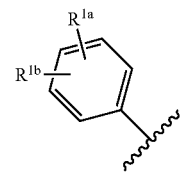

(1)

wherein $R^{1a}$ and $R^{1b}$ are selected from the group consisting of
(a) hydrogen,
(b) halogen,
(c) phenyl,
(d) —CN,
(e) —C(=O)—$R^{1c}$, wherein $R^{1c}$ is hydrogen or $C_{1-10}$ alkyl,
(f) —$C_{3-12}$ cycloalkyl, and
(g) —X—$R^{1d}$,
  wherein X is selected from the group consisting of
    (i) —O—,
    (ii) —C(=O)—,
    (iii) —S—,
    (iv) —S(=O)—, and
    (v) —S(=O)$_2$—,
  and $R^{1d}$ is selected from the group consisting of
    (i) —$C_{1-6}$ alkyl,
    (ii) —$C_{1-3}$ alkoxy,
    (iii) —$C_{3-8}$ cycloalkyl, and
    (iv) phenyl;
or $R^{1a}$ and $R^{1b}$ are linked together to form the group
  —O—$CH_2CH_2$—O— or —CH=CH—CH=CH—;
or $R^1$ is selected from the group consisting of
(2) —C(=O)$NR^{1e}R^{1f}$,
(3) —$OSO_2R^{1g}$, and
(4) —$N(R^{1g})SO_2R^{1h}$;
wherein $R^{1e}$, $R^{1f}$, $R^{1g}$ and $R^{1h}$ are independently selected from the group consisting of (a) —$C_{1-6}$alkyl,
(b) —$C_{2-6}$alkenyl,
(c) —$C_{2-6}$alkynyl,
(d) —$C_{0-6}$alkyl-$C_{3-12}$cycloalkyl,
(e) —$C_{1-6}$alkyl-di($C_{3-12}$cycloalkyl),
(f) —$C_{0-6}$alkyl-aryl,
(g) —$C_{0-6}$alkenyl-aryl,
(h) —$C_{0-6}$alkyl-di(aryl), and
(i) —$C_{0-6}$alkyl-heteroaryl;
  wherein said heteroaryl is selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl and benzoxazolyl,
  and said aryl is selected from the group consisting of phenyl and napthyl,
  and said alkyl, alkenyl, cycloalkyl, aryl and heteroaryl are unsubstituted or substituted with one or more
    (i) halo,
    (ii) —OH,
    (iii) =O,
    (iv) —CN,
    (v) —$CF_3$,
    (vi) —$OCF_3$,
    (vii) —$C_{1-6}$ alkyl,
    (viii) —$C_{1-3}$ alkoxy,
    (ix) —$C_{3-12}$ cycloalkyl,
    (x) phenyl,
    (xi) —$N_3$, or
    (xii) —X—$R^d$,
  or $R^{1e}$ and $R^{1f}$ are linked with the nitrogen atom to which they are attached to form a 5-7 membered heterocyclic ring,
$R^2$ is selected from the group consisting of
  (1) hydrogen, and
  (2) —$C_{1-6}$ alkyl; and
$R^{3a}$, $R^{3b}$ and $R^{3c}$ are independently selected from the group consisting of
  (1) hydrogen,
  (2) halo,
  (3) —OH,
  (4) —CN,
  (5) —$CF_3$,
  (6) —$OCF_3$,
  (7) —$C_{1-6}$ alkyl,
  (8) —$C_{1-3}$ alkoxy,
  (9) —$C_{3-12}$ cycloalkyl, and
  (10) —NHC(=O)$CH_2$$NR^{1a}R^{1b}$;

and pharmaceutically acceptable salts thereof, and individual enantiomers and diastereomers thereof.

In some embodiments, the invention is directed to compounds of formula (I) wherein $R^2$ is —$C_{1-6}$ alkyl, preferably methyl.

In some embodiments, the invention is directed to compounds of formula (I) wherein wherein $R^{6a}$ and $R^{6c}$ are hydrogen, and $R^{6b}$ is selected from the group consisting of hydrogen and halogen (preferably fluoro).

In some embodiments, the invention is directed to compounds of formula (I) wherein $R^1$ is aryl (preferably phenyl), which is unsubstituted or substituted with cyano. In other embodiments, the invention is directed to compounds of formula (I) wherein $R^1$ is selected from the group consisting of (1) —C(=O)$NR^{1e}R^{1f}$,
(2) —$OSO_2R^{1g}$, and
(3) —N($R^{1g}$)$SO_2R^{1h}$.

For example, in certain embodiments the invention is directed to compounds of formula (I) wherein $R^1$ is —C(=O)$NR^{1e}R^{1f}$, and $R^{1e}R^{1f}$, and $R^{1e}$ and $R^{1f}$ are preferably each selected from the group consisting of
  (a) —$C_{1-6}$alkyl,
  (b) —$C_{2-6}$alkenyl,
  (c) —$C_{2-6}$alkynyl, and
  (d) —$C_{0-6}$alkyl-$C_{3-12}$cycloalkyl.

In other embodiments, $R^1$=—$OSO_2R^{1g}$, and wherein $R^{1g}$ is preferably —$C_{0-6}$alkyl-aryl, for example benzyl, wherein the aryl group is unsubstituted or substituted with one or more halo (preferably flouro), —CN, —$CF_3$, —$C_{1-6}$ alkyl, —$C_{3-12}$ cycloalkyl and phenyl.

As used herein, the term "alkyl," by itself or as part of another substituent, means a saturated straight or branched chain hydrocarbon radical having the number of carbon atoms designated (e.g., $C_{1-10}$ alkyl means an alkyl group having from one to ten carbon atoms). Preferred alkyl groups for use in the invention are $C_{1-6}$ alkyl groups, having from one to six carbon atoms. Exemplary alkyl groups include methyl, ethyl, n-propyl, isopropyl, n-butyl, isobutyl, tert-butyl, pentyl, hexyl, and the like.

As used herein, the term "alkoxy," by itself or as part of another substituent, means the group —O— alkyl, wherein alkyl is defined above, having the number of carbon atoms designated (e.g., $C_{1-6}$ alkoxy means an alkoxy group having from one to six carbon atoms. Exemplary preferred alkoxy groups include methoxy, ethoxy, propoxy, butoxy, sec-butoxy and pentoxy. Especially preferred alkoxy groups are $C_{1-3}$ alkoxy.

As used herein, the term "alkenyl," by itself or as part of another substituent, means a straight or branched chain hydrocarbon radical having a single carbon-carbon double bond and the number of carbon atoms designated (e.g., $C_{2-10}$ alkenyl means an alkenyl group having from two to ten carbon atoms). Preferred alkenyl groups for use in the invention are $C_{2-6}$ alkenyl groups, having from two to six carbon atoms. Exemplary alkenyl groups include ethenyl and propenyl.

As used herein, the term "alkynyl," by itself or as part of another substituent, means a straight or branched chain hydrocarbon radical having a single carbon-carbon triple bond and the number of carbon atoms designated (e.g., $C_{2-10}$ alkynyl means an alkynyl group having from two to ten carbon atoms). Preferred alkynyl groups for use in the invention are $C_{2-6}$ alkynyl groups, having from two to six carbon atoms. Exemplary alkynyl groups include ethynyl and propynyl.

As used herein, the term "cycloalkyl," by itself or as part of another substituent, means a saturated monocyclic, polycyclic or bridged cyclic hydrocarbon radical having the number of carbon atoms designated (e.g., $C_{3-12}$ cycloalkyl means a cycloalkyl group having from three to twelve carbon atoms). Exemplary monocyclic cycloalkyl groups are $C_{3-8}$ cycloalkyl groups, including cyclopropyl, cyclobutyl, cyclopentyl, cyclohexyl and the like. Exemplary bridged cycloalkyl groups include adamantyl and norbornyl.

As used herein, the term "aryl," by itself or as part of another substituent, means an aromatic or cyclic radical having the number of carbon atoms designated (e.g., $C_{6-10}$ aryl means an aryl group having from six to ten carbons atoms). Preferred aryl groups for use in the invention include phenyl and naphthyl.

The term "halo" or "halogen" includes fluoro, chloro, bromo and iodo.

As used herein, the term "heteroaryl," by itself or as part of another substituent, means an aromatic cyclic group having at least one ring heteroatom (O, N or S). Exemplary heteroaryl groups for use in the invention include furyl, pyranyl, benzofuranyl, isobenzofuranyl, chromenyl, thienyl, benzothiophenyl, pyrrolyl, pyrazolyl, imidazolyl, pyridyl,pyrazinyl, pyrimidinyl, pyridazinyl, indolyl, indazolyl, benzimidazolyl, quinolyl and isoquinolyl. When a heteroaryl group as defined herein is substituted, the substituent may be bonded to a ring carbon atom of the heteroaryl group, or on a ring heteroatom (i.e., a nitrogen, oxygen or sulfur), which has a valence which permits substitution. Preferably, the substituent is bonded to a ring carbon atom.

Some of the compounds of the instant invention have at least one asymmetric center. Additional asymmetric centers may be present depending upon the nature of the various substituents on the molecule. Compounds with asymmetric centers give rise to enantiomers (optical isomers), diastereomers (configurational isomers) or both, and it is intended that all of the possible enantiomers and diastereomers in mixtures and as pure or partially purified compounds are included within the scope of this invention. The present invention is meant to encompass all such isomeric forms of these compounds.

The independent syntheses of the enantiomerically or diastereomerically enriched compounds, or their chromatographic separations, may be achieved as known in the art by appropriate modification of the methodology disclosed herein. Their absolute stereochemistry may be determined by the x-ray crystallography of crystalline products or crystalline intermediates that are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods using chiral stationary phases, which methods are well known in the art.

Alternatively, any enantiomer of a compound may be obtained by stereoselective synthesis using optically pure starting materials or reagents of known configuration by methods well known in the art.

The compounds claimed in this invention can be prepared according to the following general procedure methods, and the specific examples.

The compounds claimed in this invention can be prepared according to the following general procedures.

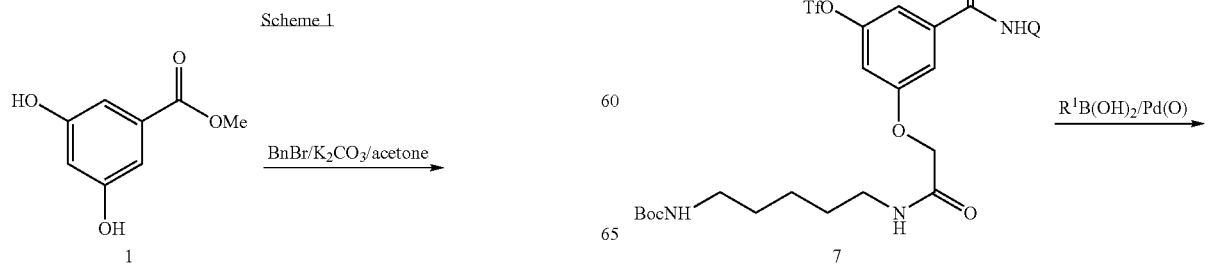

-continued

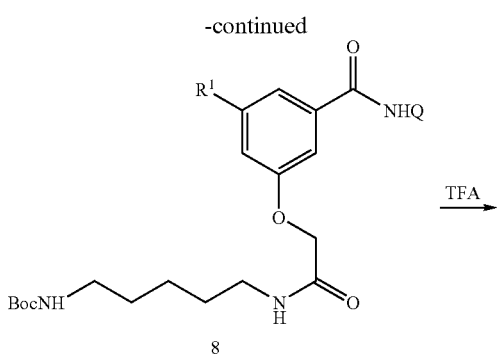
8

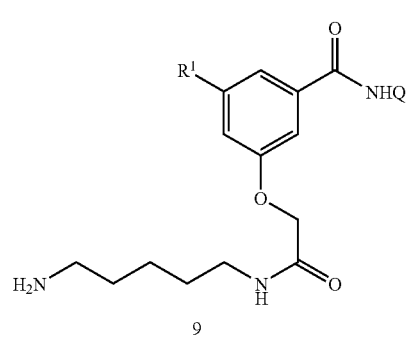
9

A variety of biphenyl-derived BACE inhibitors can be prepared according to the method outlined in scheme 1 above. The starting resorcinol derivative 1 can be protected as its mono benzyl ether by reaction with benzyl bromide in the presence of an acid scavenger such as potassium carbonate in acetone to form 2. Intermediates 2 can be revealed by the action of a strong base such as sodium hydroxide and the resulting acid can be coupled to an appropriately substituted amine counterpart using an amide coupling agent such as the BOP reagent with a trialkylamine to form 3. The phenolic hydroxyl group can be activated for coupling by conversion to the corresponding triflate ester using triflic anhydride and a tertiary amine such as Hunig's base to provide 4. The benzyl ether protecting group can be removed using a palladium catalyst under an atmosphere of hydrogen to provide 5 which can be alkylated with a 2-haloacetate ester such as benzyl 2-bromoacetate in the presence of a base suitable for deprotonation such as sodium hydride. The resulting phenoxy acetate ester can be deprotected using standard hydrogenation conditions to provide 6. Carboxylic acid 6 can be coupled to a mono-Boc protected 1,5-pentanediamine reagent by reaction with a trialkylamine and an amide coupling agent such as the BOP reagent to form 7. This triflate can be coupled to a variety of boronic acids using standard protocol for such Suzuki coupling reactions to provide a penultimate intermediate which can be deprotected with a strong acid such as TFA to afford the target compounds 9.

Scheme 2

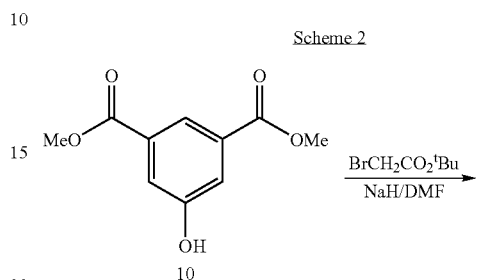
10

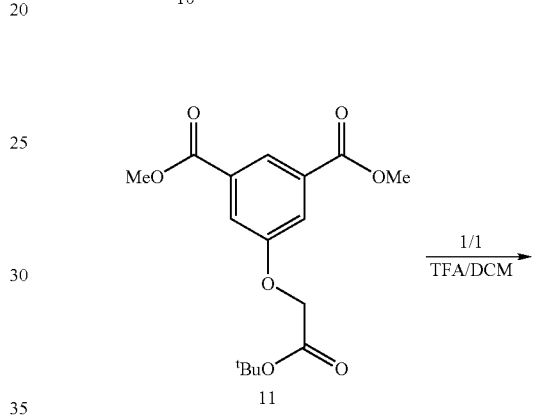
11

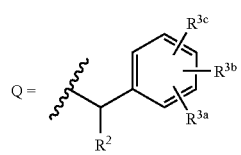

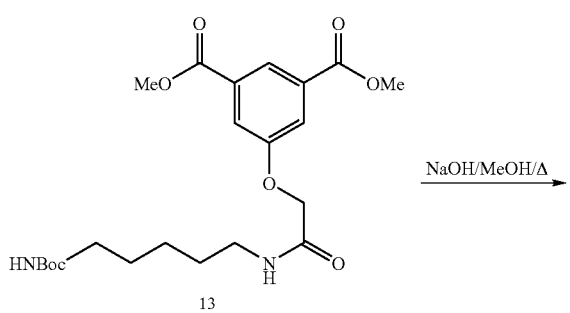
12

13

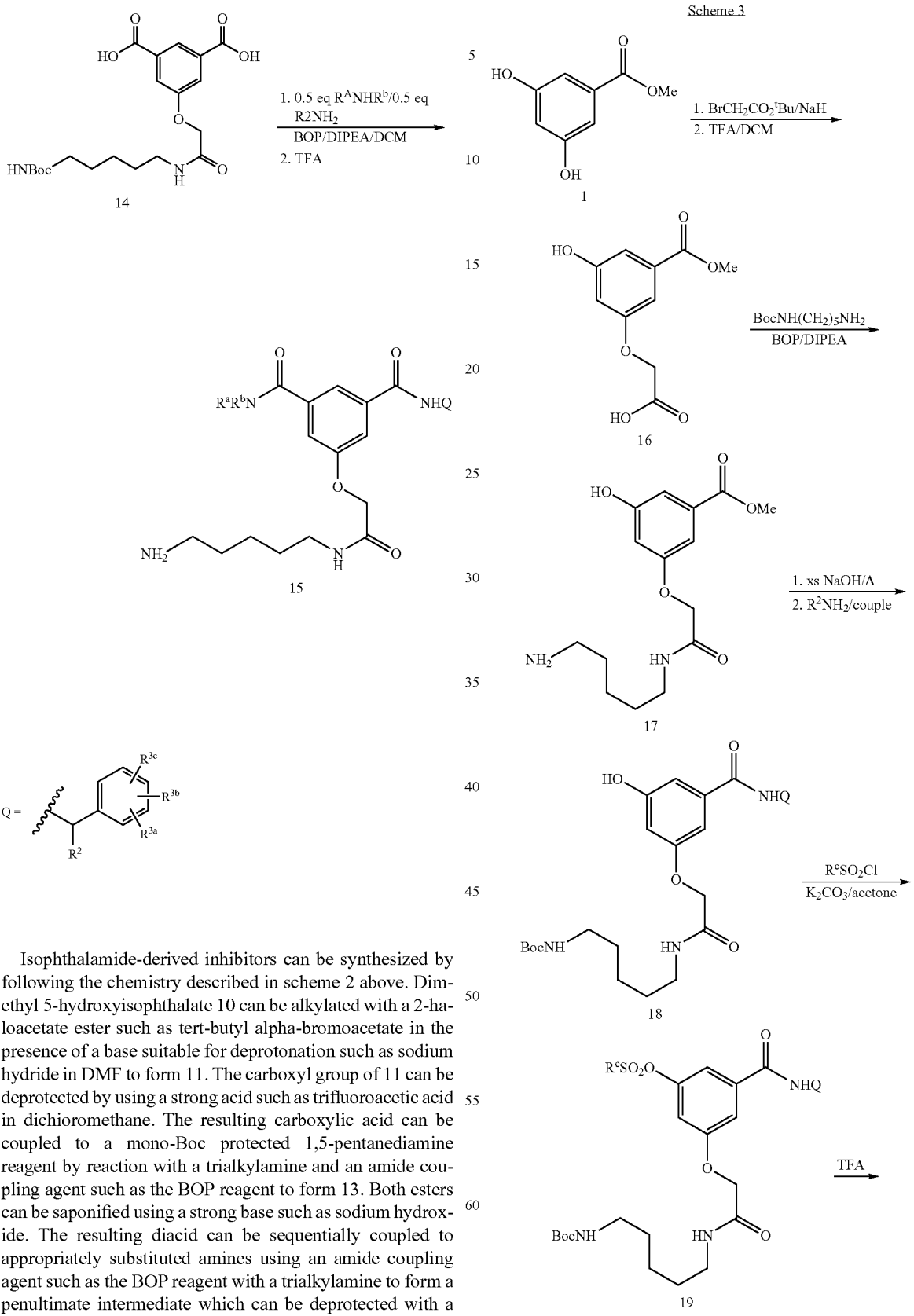

Scheme 3

Isophthalamide-derived inhibitors can be synthesized by following the chemistry described in scheme 2 above. Dimethyl 5-hydroxyisophthalate 10 can be alkylated with a 2-haloacetate ester such as tert-butyl alpha-bromoacetate in the presence of a base suitable for deprotonation such as sodium hydride in DMF to form 11. The carboxyl group of 11 can be deprotected by using a strong acid such as trifluoroacetic acid in dichloromethane. The resulting carboxylic acid can be coupled to a mono-Boc protected 1,5-pentanediamine reagent by reaction with a trialkylamine and an amide coupling agent such as the BOP reagent to form 13. Both esters can be saponified using a strong base such as sodium hydroxide. The resulting diacid can be sequentially coupled to appropriately substituted amines using an amide coupling agent such as the BOP reagent with a trialkylamine to form a penultimate intermediate which can be deprotected with a strong acid such as TFA to provide the target compounds 15.

-continued

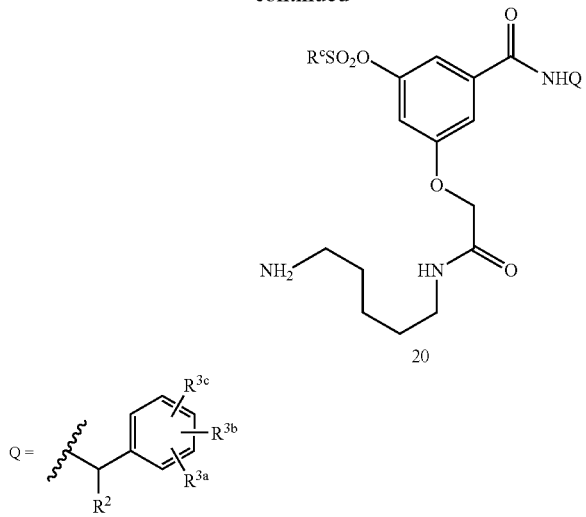

A variety of sulfonylated inhibitors can be prepared according to the method outlined in scheme 3 above. The starting resorcinol derivative 1 can be mono alkylated with a 2-haloacetate ester such as tert-butyl alpha-bromoacetate in the presence of a base suitable for deprotonation such as sodium hydride in TBF to form 16. The carboxy functional group of 16 can be deprotected by the action of a strong acid such as trifluoroacetic acid in dichloromethane. The resulting carboxylic acid can then be coupled to a mono-Boc protected 1,5-pentanediamine reagent by reaction with a trialkylamine and an amide coupling agent such as the BOP reagent to form 17. The methyl ester functional group can be saponified using a strong base such as sodium hydroxide. The resulting benzoic acid can be coupled to an appropriately substituted amine counterpart using an amide coupling agent such as the BOP reagent with a trialkylamine to form 18.

The phenolic hydroxyl group of 18 can then be sulfonylated by exposure to an appropriately substituted sulfonyl chloride and an acid scavenger such as potassium carbonate to form 19, which can then be deprotected using a strong acid such as HCl gas or TFA in dichloromethane to provide the final targets 20.

The term "substantially pure" means that the isolated material is at least 90% pure, and preferably 95% pure, and even more preferably 99% pure as assayed by analytical techniques known in the art.

The term "pharmaceutically acceptable salts" refers to salts prepared from pharmaceutically acceptable non-toxic bases or acids including inorganic or organic bases and inorganic or organic acids. The compounds of the invention may be mono, di or tris salts, depending on the number of acid functionalities present in the free base form of the compound. Free bases and salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. When the compound of the present invention is basic, salts may be prepared from pharmaceutically acceptable non-toxic acids, including inorganic and organic acids. Such acids include acetic, trifluoroacetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, trifluoroacetic, maleic, phosphoric, sulfuric, fumaric, and tartaric acids.

The present invention is directed to the use of the compounds disclosed herein as inhibitors of β-secretase enzyme activity or β-site amyloid precursor protein-cleaving enzyme ("BACE") activity, in a patient or subject such as a mammal in need of such inhibition, comprising the administration of an effective amount of the compound. The terms "β-secretase enzyme," "β-site amyloid precursor protein-cleaving enzyme," and "BACE" are used interchangeably in this specification. In addition to humans, a variety of other mammals can be treated according to the method of the present invention.

The present invention is further directed to a method for the manufacture of a medicament or a composition for inhibiting β-secretase enzyme activity in humans and animals comprising combining a compound of the present invention with a pharmaceutical carrier or diluent.

The compounds of the present invention have utility in treating, ameliorating, controlling or reducing the risk of Alzheimer's disease. For example, the compounds may be useful for the prevention of dementia of the Alzheimer's type, as well as for the treatment of early stage, intermediate stage or late stage dementia of the Alzheimer's type. The compounds may also be useful in treating, ameliorating, controlling or reducing the risk of diseases mediated by abnormal cleavage of amyloid precursor protein (also referred to as APP), and other conditions that may be treated or prevented by inhibition of β-secretase. Such conditions include mild cognitive impairment, Trisomy 21 (Down Syndrome), cerebral amyloid angiopathy, degenerative dementia, Hereditary Cerebral Hemorrhage with Amyloidosis of the Dutch-Type (HCHWA-D), Creutzfeld-Jakob disease, prion disorders, amyotrophic lateral sclerosis, progressive supranuclear palsy, head trauma, stroke, Down syndrome, pancreatitis, inclusion body myositis, other peripheral amyloidoses, diabetes and atherosclerosis.

The subject or patient to whom the compounds of the present invention is administered is generally a human being, male or female, in whom inhibition of β-secretase enzyme activity is desired, but may also encompass other mammals, such as dogs, cats, mice, rats, cattle, horses, sheep, rabbits, monkeys, chimpanzees or other apes or primates, for which inhibition of β-secretase enzyme activity or treatment of the above noted disorders is desired.

The compounds of the present invention may be used in combination with one or more other drugs in the treatment of diseases or conditions for which the compounds of the present invention have utility, where the combination of the drugs together are safer or more effective than either drug alone. Additionally, the compounds of the present invention may be used in combination with one or more other drugs that treat, prevent, control, ameliorate, or reduce the risk of side effects or toxicity of the compounds of the present invention. Such other drugs may be administered, by a route and in an amount commonly used therefor, contemporaneously or sequentially with the compounds of the present invention. Accordingly, the pharmaceutical compositions of the present invention include those that contain one or more other active ingredients, in addition to the compounds of the present invention. The combinations may be administered as part of a unit dosage form combination product, or as a kit or treatment protocol wherein one or more additional drugs are administered in separate dosage forms as part of a treatment regimen.

Examples of combinations of the compounds of the present invention with other drugs in either unit dose or kit form include combinations with: anti-Alzheimer's agents, for example other beta-secretase inhibitors or gamma-secretase inhibitors; growth hormone secretagogues; HMG-CoA reductase inhibitors; NSAED's including ibuprofen; vitamin E; anti-amyloid antibodies; CB-1 receptor antagonists or CB-1 receptor inverse agonists; antibiotics such as doxycycline and rifampin; N-methyl-D-aspartate (NMDA) receptor antagonists, such as memantine; cholinesterase inhibitors such as galantamine, rivastigmine, donepezil, and tacrine; or other drugs that affect receptors or enzymes that either increase the efficacy, safety, convenience, or reduce unwanted side effects or toxicity of the compounds of the present invention. The foregoing list of combinations is illustrative only and not intended to be limiting in any way.

The term "composition" as used herein is intended to encompass a product comprising specified ingredients in predetermined amounts or proportions, as well as any product which results, directly or indirectly, from combination of the specified ingredients in the specified amounts. This term in relation to pharmaceutical compositions is intended to encompass a product comprising one or more active ingredients, and an optional carrier comprising inert ingredients, as well as any product which results, directly or indirectly, from combination, complexation or aggregation of any two or more of the ingredients, or from dissociation of one or more of the ingredients, or from other types of reactions or interactions of one or more of the ingredients. In general, pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. Accordingly, the pharmaceutical compositions of the present invention encompass any composition made by admixing a compound of the present invention and a pharmaceutically acceptable carrier.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period.

Compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Other pharmaceutical compositions include aqueous suspensions, which contain the active materials in admixture with excipients suitable for the manufacture of aqueous suspensions. In addition, oily suspensions may be formulated by suspending the active ingredient in a vegetable oil, for example arachis oil, olive oil, sesame oil or coconut oil, or in a mineral oil such as liquid paraffin. Oily suspensions may also contain various excipients. The pharmaceutical compositions of the invention may also be in the form of oil-in-water emulsions, which may also contain excipients such as sweetening and flavoring agents.

The pharmaceutical compositions may be in the form of a sterile injectable aqueous or oleaginous suspension, which may be formulated according to the known art, or may be administered in the form of suppositories for rectal administration of the drug.

The compounds of the present invention may also be administered by inhalation, by way of inhalation devices known to those skilled in the art, or by a transdermal patch.

By "pharmaceutically acceptable" it is meant the carrier, diluent or excipient must be compatible with the other ingredients of the formulation and not deleterious to the recipient thereof.

The terms "administration of" or "administering a" compound should be understood to mean providing a compound of the invention to the individual in need of treatment in a form that can be introduced into that individual's body in a therapeutically useful form and therapeutically useful amount, including, but not limited to: oral dosage forms, such as tablets, capsules, syrups, suspensions, and the like; injectable dosage forms, such as IV, IM, or IP, and the like; transdermal dosage forms, including creams, jellies, powders, or patches; buccal dosage forms; inhalation powders, sprays, suspensions, and the like; and rectal suppositories.

The terms "effective amount" or "therapeutically effective amount" means the amount of the subject compound that will elicit the biological or medical response of a tissue, system, animal or human that is being sought by the researcher, veterinarian, medical doctor or other clinician. As used herein, the term "treatment" refers to the treatment of the mentioned conditions, particularly in a patient who demonstrates symptoms of the disease or disorder.

As used herein, the term "treatment" or "treating" means any administration of a compound of the present invention and includes (1) inhibiting the disease in an animal that is experiencing or displaying the pathology or symptomatology of the diseased (i.e., arresting further development of the pathology and/or symptomatology), or (2) ameliorating the disease in an animal that is experiencing or displaying the pathology or symptomatology of the diseased (i.e., reversing the pathology and/or symptomatology). The term "controlling" includes preventing treating, eradicating, ameliorating or otherwise reducing the severity of the condition being controlled.

The compositions containing compounds of the present invention may conveniently be presented in unit dosage form and may be prepared by any of the methods well known in the art of pharmacy. The term "unit dosage form" is taken to mean a single dose wherein all active and inactive ingredients are combined in a suitable system, such that the patient or person administering the drug to the patient can open a single container or package with the entire dose contained therein, and does not have to mix any components together from two or more containers or packages. Typical examples of unit dosage forms are tablets or capsules for oral administration, single dose vials for injection, or suppositories for rectal administration. This list of unit dosage forms is not intended to be limiting in any way, but merely to represent typical examples of unit dosage forms.

The compositions containing compounds of the present invention may conveniently be presented as a kit, whereby two or more components, which may be active or inactive ingredients, carriers, diluents, and the like, are provided with instructions for preparation of the actual dosage form by the patient or person administering the drug to the patient. Such kits may be provided with all necessary materials and ingredients contained therein, or they may contain instructions for using or making materials or components that must be obtained independently by the patient or person administering the drug to the patient.

When treating, ameliorating, controlling or reducing the risk of Alzheimer's disease or other diseases for which compounds of the present invention are indicated, generally satisfactory results are obtained when the compounds of the present invention are administered at a daily dosage of from about 0.1 mg to about 100 mg per kg of animal body weight, preferably given as a single daily dose or in divided doses two to six times a day, or in sustained release form. The total daily dosage is from about 1.0 mg to about 2000 mg, preferably from about 0.1 mg to about 20 mg per kg of body weight. In the case of a 70 kg adult human, the total daily dose will generally be from about 7 mg to about 1,400 mg. This dosage regimen may be adjusted to provide the optimal therapeutic response. The compounds may be administered on a regimen of 1 to 4 times per day, preferably once or twice per day.

Specific dosages of the compounds of the present invention, or pharmaceutically acceptable salts thereof, for administration include 1 mg, 5 mg, 10 mg, 30 mg, 80 mg, 100 mg, 150 mg, 300 mg and 500 mg. Pharmaceutical compositions of the present invention may be provided in a formulation comprising about 0.5 mg to 1000 mg active ingredient; more preferably comprising about 0.5 mg to 500 mg active ingredient; or 0.5 mg to 250 mg active ingredient; or 1 mg to 100 mg active ingredient. Specific pharmaceutical compositions useful for treatment may comprise about 1 mg, 5 mg, 10 mg, 30 mg, 80 mg, 100 mg, 150 mg, 300 mg and 500 mg of active ingredient.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The utility of the compounds in accordance with the present invention as inhibitors of β-secretase enzyme activity may be demonstrated by methodology known in the art. Enzyme inhibition is determined as follows.

FRET Assay: A homogeneous end point fluorescence resonance energy transfer (FRET) assay is employed with the substrate ([TAMRA-5-CO-EEISEVNLDAEF-NHQSY] QFRET), which is cleaved by BACE 1 to release the fluorescence from TAMRA. The Km of the substrate is not determined due to the limit of solubility of the substrate. A typical reaction contains approximately 30 nM enzyme, 1.25 μM of the substrate, and buffer (50 mM NaOAc, pH 4.5, 0.1 mg/ml BSA, 0.2% CHAPS, 15 mM EDTA and 1 mM deferoxamine) in a total reaction volume of 100 μl. The reaction is proceeded for 30 min and the liberation of TAMRA fragment is measured in a 96-well plate LJL Analyst AD using an excitation wavelength of 530 nm and an emission wavelength of 580 nm. Under these conditions, less than 10% of substrate is processed by BACE 1. The enzyme used in these studies is soluble (transmembrane domain and cytoplasmic extension excluded) human protein produced in a baculovirus expression system. To measure the inhibitory potency of compounds, solutions of inhibitor in DMSO (four concentrations of the inhibitors are prepared: 1 mM, 100 μM, 10 μM, 1 μM) are included in the reactions mixture (final DMSO concentration is 0.8%). All experiments are conducted at room temperature using the standard reaction conditions described above. To determine the $IC_{50}$ of the compound, competitive equation $V0/Vi=1+[I]/[IC50]$ is used to predict the inhibitory potency of the compounds. The errors in reproducing the dissociation constants are typically less than two-fold.

HPLC assay: A homogeneous end point HPLC assay is employed with the substrate (coumarin-CO-REVNFE-VEFR), which is cleaved by BACE 1 to release the N-terminal fragment attached with coumarin. The Km of the substrate is greater than 100 μM and can not be determined due to the limit of solubility of the substrate. A typical reaction contains approximately 2 nM enzyme, 1.0 μM of the substrate, and buffer (50 mM NaOAc, pH 4.5, 0.1 mg/ml BSA, 0.2% CHAPS, 15 mM EDTA and 1 mM deferoxamine) in a total reaction volume of 100 μl. The reaction is proceeded for 30 min and the reaction is stopped by the addition of 25 μL of 1 M Tris-HCl, pH 8.0. The resulting reaction mixture is loaded on the HPLC and the product is separated from substrate with 5 min linear gradient. Under these conditions, less than 10% of substrate is processed by BACE 1. The enzyme used in these studies is soluble (transmembrane domain and cytoplasmic extension excluded) human protein produced in a baculovirus expression system. To measure the inhibitory potency for compounds, solutions of inhibitor in DMSO (12 concentrations of the inhibitors are prepared and the concentration rage is dependent on the potency predicted by FRET) are included in the reaction mixture (final DMSO concentration is 10%). All experiments are conducted at rt using the standard reaction conditions described above. To determine the $IC_{50}$ of the compound, four parameters equation is employed for curve fitting. The errors in reproducing the dissociation constants are typically less than two-fold.

In particular, the compound of the following example had activity in inhibiting the beta-secretase enzyme in the aforementioned assays, generally with an IC50 from about 1 nM to 100 μM. Such a result is indicative of the intrinsic activity of the compounds of the invention in use as inhibitors of the beta-secretase enzyme activity.

Several methods for preparing the compounds of this invention are illustrated in the schemes and example herein. Starting materials are made according to procedures known in the art or as illustrated herein. The following example is provided so that the invention might be more fully understood. This example is illustrative only and should not be construed as limiting the invention in any way.

EXAMPLE

3-{2-[(5-aminopentyl)amino]-2-oxoethoxy}-5-({[(1R)-1-(4-fluorophenyl)ethyl]amino}carbonyl)phenyl phenylmethanesulfonate Step A: Methyl 3-(2-tert-butoxy-2-oxoethoxy)-5-hydroxybenzoate

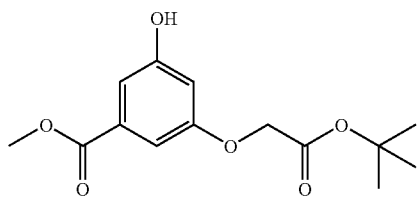

To a 0° C. solution containing 3.36 g (20.0 mmol) of methyl 3,5-dihydroxy benzoate (Aldrich) in 100 mL of THF was added 4.4 g (20.0 mmol) of 15-crown-5 then 480 mg (20.0 mmol) of NaH (95%). The solution was stirred for 30 min before the addition of 3.0 mL (20.0 mmol) of tert-butylbromoacetate. The reaction mixture was allowed to warm slowly to ambient temperature before it was diluted with ether (100 mL) and quenched with saturated NH₄Cl (50 mL). The organic phase was separated and washed with water (25 mL) then brine (25 mL). The organic solution was dried over MgSO₄, concentrated and chromatographed (2:3 EtOAc/Hexanes) to afford the desired mono-alkylated phenol. ¹H NMR (CDCl₃) δ 7.17 (s, 1H), 7.08 (s, 1H), 6.66 (t, J=2.4 Hz, 1H), 6.04 (s, 1H), 4.54 (s, 2H), 3.88 (s, 3H), 1.55 (s, 9H). ¹³C NMR (CDCl₃) δ 168.3, 166.9, 159.1, 157.2, 132.2, 110.5, 107.9, 107.0, 83.1, 65.9, 52.5, 28.2. HRMS (calculated for M+Na)=305.0995. Found=305.0992.

Step B: (3-Hydroxy-5-(methoxycarbonyl)phenoxy)acetic acid

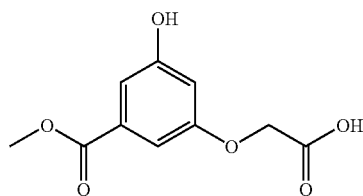

To a 0° C. solution containing 1.90 g (6.73 mmol) of the ester from step A in 20 mL of dichloromethane was treated with 10 mL of TFA. The resulting solution was stirred at rt for 2 h after which time the solvents were removed in vacuo to leave the desired carboxylic acid as a white solid. ¹H NMR (CD₃OD) δ 7.06 (s, 1H), 7.03 (s, 1H), 6.60 (t, J=2.3 Hz, 1H), 6.04 (s, 1H), 4.87 (bs, 2H), 3.86 (s, 3H),. ¹³C NMR (CD₃OD) δ 171.1, 167.0, 159.3, 158.7, 132.0, 109.6, 106.7, 106.1, 64.8, 51.4. HRMS (calculated for M +Na)=249.0369. Found=249.0356.

Step C: Methyl 3-[2-({5-[(tert-butoxycarbonyl)amino]pentyl}amino)-2-oxoethy-oxy]-5-hydroxybenzoate

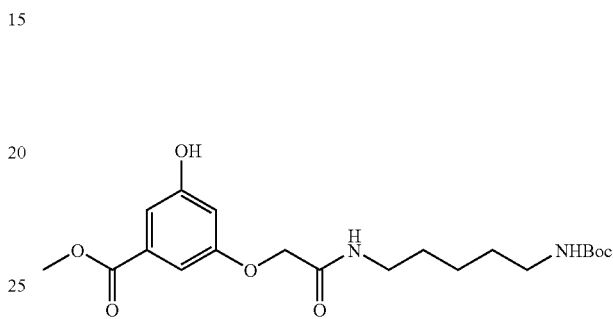

To a solution containing 650 mg (2.87 mmol) of the acid from step B in 20 mL of dichloromethane was added 581 mg (2.87 mmol) of N-Boc-1,5-pentanediamine, 1.27 g (2.87 mmol) of BOP reagent and 1.5 mL (8.61 mmol) of Hunig's base. The resulting solution was stirred at rt for 1 h before it was quenched with water (5 mL). The organic phase was washed with brine (10 mL), dried over MgSO₄, concentrated and chromatographed (4:1 EtOAc/Hexanes) to afford the desired amide. ¹H NMR (CDCl₃) δ 7.23 (s, 1H), 7.14 (s, 1H), 6.67 (s, 1H), 6.56 (bt, 1H), 4.72 (bs, 1H), 4.52 (s, 2H), 3.89 (s, 3H), 3.35 (q, J=6.3 Hz, 2H), 3.06 (q, J=6.6 Hz, 2H), 1.5 (m, 4H), 1.45 (s, 9H), 1.22 (m, 2H). ¹³C NMR (CDCl₃) δ 168.5, 166.8, 158.4, 158.3, 132.6, 111.0, 108.2, 106.7, 67.7, 52.5, 40.6, 38.9, 29.9, 29.2, 28.6, 24.0. HRMS (calculated)=411.2126. Found=411.2125.

Step D: tert-butyl[5-({[3-({[(1R)-1-(4-fluorophenyl)ethyl]amino}carbonyl)-5-hydroxyphenoxy]acetyl}amino)pentyl] carbamate

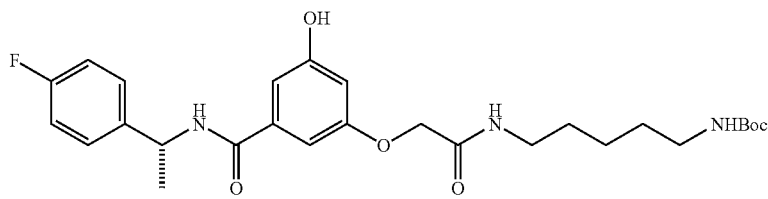

To a solution of 920 mg (2.03 mmol) of the ester from step C in 10 mL of methanol and 10 mL of THF was added 3.0 mL (3.0 mmol) of 1N NaOH. The reaction mixture was heated at 50° C. for 5 h, cooled to 0° C. and neutralized with 1 N HCl. The solvents were evaporated and the residue was azeotroped with toluene. The crude benzoic acid was dissolved in 20 mL of dichloromethane and treated with 278 mg (2.00 mmol) of (R)-(+)-4-fluoro-α-methylbenzylamine (Lancaster Synthesis), 884 mg (2.00 mmol) of BOP reagent and 0.70 mL (4.0 mmoL) of Hunig's base. The resulting solution was stirred at rt for 30 min before it was quenched with water (5 mL). The organic phase was washed with brine (10 mL), dried over MgSO$_4$, concentrated and chromatographed (9:1 EtOAc/Hexanes) to afford the desired amide. $^1$H NMR (CD$_3$OD) δ 7.40 (dd, J=2.0, 7.4 Hz, 2H), 7.05 (t, J=8.8 Hz, 2H), 6.91 (d, J=2.0 Hz, 1H), 6.89 (t, J=2.2 Hz, 1H), 5.21 (q, J=7.0 Hz, 1H), 4.49 (s, 2H), 3.25 (t, J=7.0 Hz, 2H), 1.58 (d, J=7.0 Hz, 3H), 1.57-1.46 (m, 4H), 1.45 (s, 9H), 1.25 (m, 2H). $^{13}$C NMR (CD$_3$OD) δ 169.5, 168.0, 163.2, 160.8, 159.0, 158.8, 140.1, 136.9, 127.9, 127.8, 114.9, 114.7, 108.0, 105.0, 104.7, 78.6, 67.1, 48.8, 40.0, 38.8, 29.3, 28.9, 27.5, 23.8, 20.9. HRMS (calculated)=518.2661. Found=518.2677.

Step E: 3-{2-[(5-aminopentyl)amino]-2-oxoethoxy}-5-({[(1R)-1-(4-fluorophenyl) ethyl]amino}carbonyl)phenyl phenylmethanesulfonate:

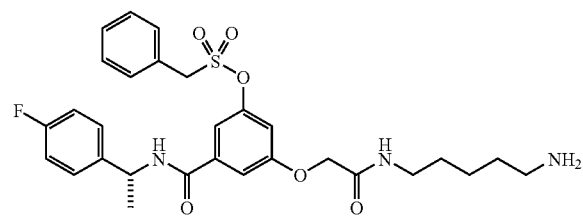

To a solution of 150 mg (0.290 mmol) of the phenol from step D in 15 mL of acetone was added 55 mg (0.29 mmol) of benzylsulfonyl chloride and 60 mg (0.44 mmol) of K$_2$CO$_3$. The resulting mixture was heated at 55° C. for 17 h before it was cooled and the solvent was removed under reduced pressure. The residue was covered with 50 mL of ether and washed with water (3×10 mL) then brine (10 mL). The organic phase was dried over MgSO$_4$ and concentrated to afford the crude sulfonate ester that was immediately redissolved in 10 mL of CH$_2$Cl$_2$ and treated with 2 mL of TFA. The reaction mixture was stirred at ambient temperature for 3 h, concentrated and the residue was subjected to reverse phase chromatography to afford the desired compound as the mono TFA salt. $^1$H NMR (CD$_3$OD) δ 7.51 (m, 2H), 7.42 (m, 6H), 7.28 (t, J=1.5 Hz, 1H), 7.07 (t, J=8.8 Hz, 2H), 6.95 (t, J=2.2 Hz, 1H), 5.19 (q, J=7.0 Hz, 1H), 4.78 (s, 2H), 4.55 (s, 2H), 3.31 (m, 4H), 2.86 (t, 7.6 Hz, 2H), 1.57 (m, 2H), 1.51 (d, J=7.0 Hz, 3H), 1.31 (m, 2H). 13C NMR (CD$_3$OD) δ 169.1, 166.2, 160.9, 158.8, 150.2, 137.3, 131.0, 129.0, 128.6, 127.97, 127.94, 127.8, 115.0, 114.8, 114.1, 112.4, 112.1, 67.3, 56.4, 49.1, 39.3, 38.4, 28.7, 26.9, 23.3, 20.8. HRMS (calculated)=572.2225. Found=572.2212.

The following abbreviations are used throughout the text:
Me: methyl
Bn: benzyl
Ac: acetyl
THF: tetrahydrofuran
DMSO: dimethylsulfoxide
EDTA: ethylene diamine tetraacetic acid
Boc: tert-butyloxy carbonyl
BOP: benzotriazol-1-yloxy-tris(dimethylamino)phosphonium hexafluorophosphate
CHAPS: 3-[(3-cholamidopropyl)dimethylammonio]-2-hydroxy-1-propanesulfonate
DIPEA: diisopropylethylamine
DCM: dichloromethane
BSA: bovine serum albumin
Tf: tri-fluoromethylsulfonyl
TFA: trifluoroacetic acid
rt: room temperature
HPLC: high performance liquid chromatography The following compounds were prepared in a manner similar to the title compounds of a the foregoing examples using appropriate starting materials and reagents:

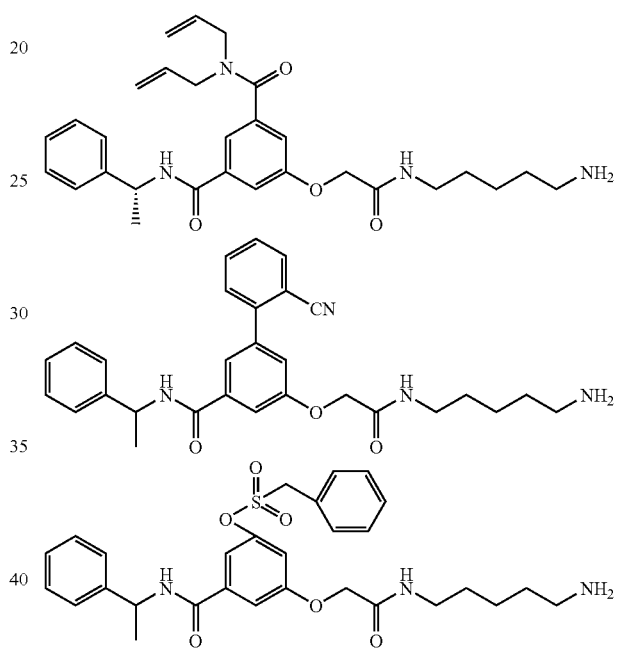

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. It is intended, therefore, that the invention be defined by the scope of the claims that follow and that such claims be interpreted as broadly as is reasonable.

The invention claimed is:

1. A compound of formula (I):

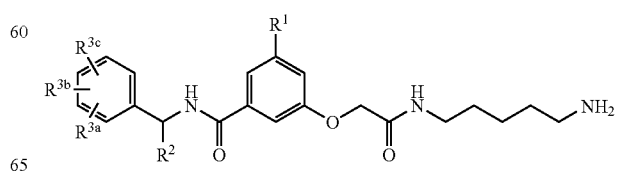

wherein
R¹ is selected from the group consisting of:

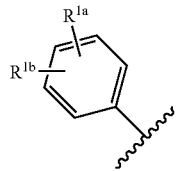
(1)

wherein R$^{1a}$ and R$^{1b}$ are selected from the group consisting of
(a) hydrogen,
(b) halogen,
(c) phenyl,
(d) —CN,
(e) —C(=O)—R$^{1c}$, wherein R$^{1c}$ is hydrogen or C$_{1-10}$ alkyl,
(f) —C$_{3-12}$ cycloalkyl, and
(g) —X—R$^{1d}$,
wherein X is selected from the group consisting of
(i) —O—,
(ii) —C(=O)—,
(iii) —S—,
(iv) —S(=O)—, and
(v) —S(=O)$_2$—,
and R$_{1d}$ is selected from the group consisting of
(i) —C$_{1-6}$ alkyl,
(ii) —C$_{1-3}$ alkoxy,
(iii) —C$_{3-12}$ cycloalkyl, and
(iv) phenyl;
or R$^{1a}$ and R$^{1b}$ are linked together to form the group —O—CH$_2$CH$_2$—O— or —CH=CH—CH=CH—;
or R¹ is selected from the group consisting of
(2) —C(=O)NR$^{1e}$R$^{1f}$,
(3) —OSO$_2$R$^{1g}$, and
(4) —N(R$^{1g}$)SO$_2$R$^{1h}$;
wherein R$^{1e}$, R$^{1f}$, R$^{1g}$ and R$^{1h}$ are independently selected from the group consisting of
(a) —C$_{1-6}$alkyl,
(b) —C$_{2-6}$alkenyl,
(c) —C$_{2-6}$alkynyl,
(d) —C$_{0-6}$alkyl-C$_{3-12}$cycloalkyl,
(e) —C$_{1-6}$alkyl-di(C$_{3-12}$cycloalkyl),
(f) —C$_{0-6}$alkyl-aryl,
(g) —C$_{0-6}$alkenyl-aryl,
(h) —C$_{0-6}$alkyl-di(aryl), and
(i) —C$_{0-6}$alkyl-heteroaryl;
wherein said heteroaryl is selected from the group consisting of pyrazinyl, pyrazolyl,
pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl and benzoxazolyl,
and said aryl is selected from the group consisting of phenyl and naphthyl,
and said alkyl, alkenyl, cycloalkyl, aryl and heteroaryl are unsubstituted or substituted with one or more
(i) halo,
(ii) —OH,
(iii) =O,
(iv) —CN,
(v) —CF$_3$,
(vi) —OCF$_3$,
(vii) —C$_{1-6}$ alkyl,
(viii) —C$_{1-3}$ alkoxy,
(ix) —C$_{3-12}$ cycloalkyl,
(x) phenyl,
(xi) —N$_3$, or
(xii) —X—R$^{1d}$,
or R$^{1e}$ and R$^{1f}$ are linked with the nitrogen atom to which they are attached to form a 5-7 membered heterocyclic ring,
R² is selected from the group consisting of
(1) hydrogen, and
(2) —C$_{1-6}$ alkyl; and
R$^{3a}$, R$^{3b}$ and R$^{3c}$ are independently selected from the group consisting of
(1) hydrogen,
(2) halo,
(3) —OH,
(4) —CN,
(5) —CF$_3$,
(6) —OCF$_3$
(7) —C$_{1-6}$ alkyl,
(8) —C$_{1-3}$ alkoxy,
(9) —C$_{3-12}$ cycloalkyl, and
(10) —NHC(=O)CH$_2$NR$^{1a}$R$^{1b}$;
and pharmaceutically acceptable salts thereof, and individual enantiomers and diastereomers thereof.

2. The compound of claim 1 wherein R² is —C$_{1-6}$ alkyl.
3. The compound of claim 2 wherein R² is methyl.
4. The compound of claim 1 wherein R$^{6a}$ and R$^{6c}$ are hydrogen, and R$^{6b}$ is selected from the group consisting of hydrogen and halogen.
5. The compound of claim 4 wherein R$^{6b}$ is halogen.
6. The compound of claim 5 wherein R$^{6b}$ is fluoro.
7. The compound of claim 1 wherein R¹ is aryl.
8. The compound of claim 7 wherein R¹ is phenyl, which is unsubstituted or substituted with cyano.
9. The compound of claim 1 wherein R¹ is selected from the group consisting of
(1) —C(=O)NR$^{1e}$R$^{1f}$,
(2) —OSO$_2$R$^{1g}$, and
(3) —N(R$^{1g}$)SO$_2$R$^{1h}$.
10. The compound of claim 9 wherein R¹ is —OSO$_2$R$^{1g}$.
11. The compound of claim 10 wherein R$^{1g}$ is phenyl.
12. A compound of claim 1 which is selected from the group consisting of

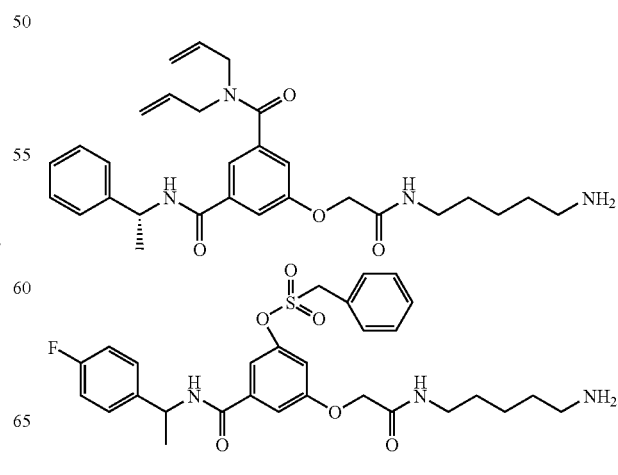

-continued
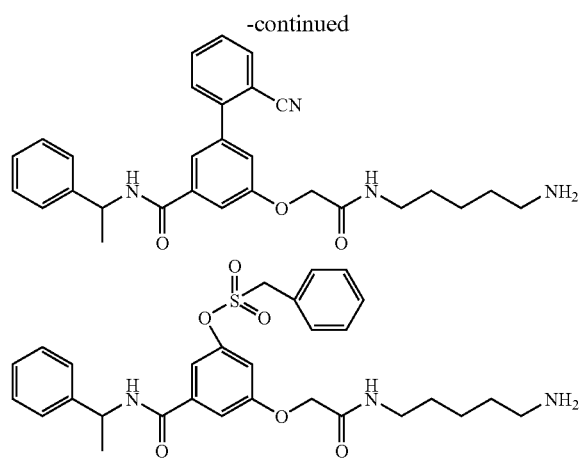
and pharmaceutically acceptable salts thereof.
13. The compound of claim 12 which is
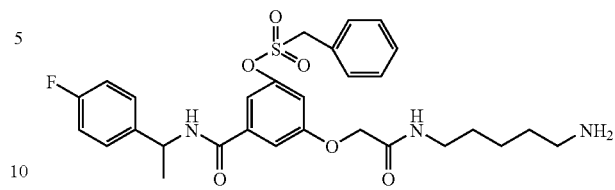
or a pharmaceutically acceptable salt thereof.
14. The pharmaceutical composition comprising a therapeutically effective amount of a compound of claim 1 or a pharmaceutically acceptable salt thereof and a pharmaceutically acceptable carrier.
* * * * *